(12) United States Patent
Ma et al.

(10) Patent No.: US 10,061,979 B2
(45) Date of Patent: Aug. 28, 2018

(54) IMAGE PROCESSING APPARATUS AND METHOD

(71) Applicant: KONINKLIJKE PHILIPS N.V., Eindhoven (NL)

(72) Inventors: Yue Ma, Shenyang (CN); YanHua Shen, Shenyang (CN); Dan Zhao, Shenyang (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/502,792

(22) PCT Filed: Sep. 22, 2015

(86) PCT No.: PCT/EP2015/071628
§ 371 (c)(1),
(2) Date: Feb. 9, 2017

(87) PCT Pub. No.: WO2016/046143
PCT Pub. Date: Mar. 31, 2016

(65) Prior Publication Data
US 2017/0236003 A1     Aug. 17, 2017

(30) Foreign Application Priority Data

Sep. 28, 2014    (WO) ................ PCT/CN2014/087677
Oct. 29, 2014    (EP) .................................... 14190871

(51) Int. Cl.
*G06K 9/00*      (2006.01)
*G06K 9/46*      (2006.01)
(Continued)

(52) U.S. Cl.
CPC .......... *G06K 9/00362* (2013.01); *A61B 6/032* (2013.01); *A61B 6/501* (2013.01);
(Continued)

(58) Field of Classification Search
CPC ............. G06K 9/00362; G06K 9/4604; G06K 2009/4666; G06K 2209/055; A61B 6/032; A61B 6/501; A61B 6/5217
(Continued)

(56) References Cited

U.S. PATENT DOCUMENTS 5,342,202 A     8/1994    Deshayes
5,825,910 A    10/1998    Vafai
(Continued)

FOREIGN PATENT DOCUMENTS

| EP | 1793350 | 6/2007 |
|---|---|---|
| JP | 2006223449 | 8/2006 |
| WO | 2012/014036 | 2/2012 |

OTHER PUBLICATIONS

Zhu, et al., "Automatic Patient Table Removal in CT Images", J. Digit. Imaging (2012).

*Primary Examiner* — Gregory F Cunningham

(57) ABSTRACT

There provides an apparatus for recognizing a head region in a CT lateral image of a subject, comprising: a deriving unit for deriving a first image representing a bone of the subject from the CT lateral image; an extracting unit for extracting a boundary curve indicating an outer contour of a region comprising at least part of the occipital bone and at least part of the cervical vertebra of the subject in the first image; and a determining unit for determining a first pixel position indicating a bottommost point of the head region of the subject, based on a shape feature parameter of the boundary curve.

20 Claims, 7 Drawing Sheets

(51) Int. Cl.
*A61B 6/03* (2006.01)
*A61B 6/00* (2006.01)

(52) U.S. Cl.
CPC .......... *A61B 6/5217* (2013.01); *G06K 9/4604* (2013.01); *G06K 2009/4666* (2013.01); *G06K 2209/055* (2013.01)

(58) Field of Classification Search
USPC ........................................................ 382/131
See application file for complete search history.

(56) References Cited

U.S. PATENT DOCUMENTS

| | | |
|---|---|---|
| 5,944,664 A | 8/1999 | Hayashi |
| 6,795,521 B2 | 9/2004 | Hsu |
| 7,133,496 B2 | 11/2006 | Wilson |
| 7,221,787 B2 | 5/2007 | Luo |
| 7,587,073 B2 | 9/2009 | Park |
| 7,756,316 B2 | 7/2010 | Odry |
| 8,050,472 B2 | 11/2011 | Lee |
| 8,433,031 B2 | 4/2013 | Nukui |
| 8,548,122 B2 | 10/2013 | Hay |
| 2005/0196031 A1 | 9/2005 | Hsieh |
| 2007/0269089 A1 | 11/2007 | Sakaida |
| 2008/0112605 A1 | 5/2008 | Hong |
| 2008/0118133 A1 | 5/2008 | Sirohey |
| 2008/0267481 A1 | 10/2008 | Nakamura |
| 2010/0049036 A1 | 2/2010 | Kimh |
| 2012/0093385 A1 | 4/2012 | Yokosawa |
| 2012/0219198 A1 | 8/2012 | Mohr |
| 2013/0267755 A1 | 10/2013 | Chebrolu |
| 2014/0100485 A1 | 4/2014 | Linguraru |
| 2014/0133726 A1* | 5/2014 | Garner ................ A61B 5/4504 382/131 |

* cited by examiner

IMAGE PROCESSING APPARATUS AND METHOD

CROSS REFERENCE TO RELATED APPLICATIONS

This application is the U.S. National Phase application under 35 U.S.C. § 371 of International Application No. PCT/EP2015/071628, filed Sep. 22, 2015, published as WO 2016/046143 on Mar. 31, 2016, which claims the benefit of European Patent Application Number 14190871.5 filed Oct. 29, 2014 and Chinese Patent Application Number PCT/CN2014/087677 filed Sep. 28, 2014. These applications are hereby incorporated by reference herein.

FIELD OF THE INVENTION

The present invention generally relates to an image processing apparatus and method, more particularly to an image processing apparatus and method to be used in CT imaging apparatus.

BACKGROUND OF THE INVENTION

During CT imaging, a subject to be imaged, e.g., a patient, usually is positioned on a support, such as a bed board and a head holder; therefore, the imaging data may comprise data for the support. However, the data for the support may be useless for a physician reviewing a CT image to diagnose a disease, or they may even get the physician into trouble.

Furthermore, during CT imaging of the head of a subject, a surview image (also known as scout image), which shows a lateral view of the head of the subject may be obtained and a user selects a region indicative of the head of the subject in the surview image, after which, further CT imaging may be performed on the selected region. In this procedure, a user needs to manually set a region of interest on the surview image, which may be time-consuming.

US 2012/219198 A1 discloses a method of selecting image data representative of a subject from an image data set comprises determining regions of image data, wherein each region of image data consists of a respective plurality of connected voxels, and selecting at least one region as being representative of the subject based upon at least one of the size and shape of the region.

US 2014/133726 discloses a method and system for automatically identifying two or more preselected anatomical features by examining pixels within images such as CT scanned images, determining appropriate measurements between such identified features. In at least one embodiment, the disclosed system can identify a first anatomical region in proximity to a basion, identify a second anatomical region in proximity to a dens, and measure the basion-dens interval (BDI).

SUMMARY OF THE INVENTION

Therefore, it would be desirable to provide an apparatus and method for automatically recognizing and, if necessary, further removing non-body parts, including a support of a subject, in each axial tomographic image. If the non-body parts have been recognized and removed from imaging data of each axial tomographic image, a 3D image without the non-body parts may be generated from the imaging data, making it convenient for a physician to review the 3D image in diagnosing a disease.

Furthermore, it would be desirable to provide an apparatus and method for automatically recognizing a head region of the subject, such as a bottommost point of the head region, in a CT lateral image of the subject. In particular, both a topmost point and a bottommost point of a head region may be determined automatically, enabling the head region of the subject to be recognized based on the determined topmost point and the determined bottommost point. In this way, a manual operation of a user may be omitted, thereby saving time.

In one aspect, there provides an image processing apparatus for processing an axial tomographic image of a subject to recognize a non-body part in the axial tomographic image. The apparatus comprises: a binarization unit for converting the axial tomographic image into a first binary image; a first identification unit for identifying one or more first connected domains from a second binary image, the second binary image being the first binary image or an image derived from the first binary image; a first feature quantity calculation unit for deriving, for each of the identified one or more first connected domains, a circularity parameter indicating a circularity of the first connected domain; a first determining unit for determining, for each of the identified one or more first connected domains, whether the first connected domain belongs to the non-body part, based on the derived circularity parameter of the first connected domain and a first predefined threshold; and a first recognizing unit for recognizing one or more regions corresponding to all of the one or more first connected domains determined as belonging to the non-body part in the axial tomographic image.

The above technical solution is based on the insight that the shape of any body part of a subject is closer to a circle than the shape of a non-body part, such as a bed board and a head holder, in a region subjected to a CT imaging examination.

In light of the foregoing, the circularity parameter is applied to distinguish non-body parts from body parts. The circularity parameter is a measure of how closely the shape of an object approaches that of a circle, which is dominated by the shape's large-scale features rather than the sharpness of its edges and corners, or the surface roughness of a manufactured object. For example, regular polygons with increasing numbers of sides may be closer to a circle than a smooth ellipse with large eccentricity.

In this way, the non-body parts may be automatically recognized and, if necessary, removed from each axial tomographic image of a subject, and a 3D image without the non-body parts may be reconstructed based on the axial tomographic images. The reconstructed 3D image will not confuse or disturb the physician reviewing the image in diagnosing a disease again.

In a preferable embodiment, the image processing apparatus comprises a first deriving unit for deriving the second binary image from the first binary image, wherein the first deriving unit comprises: a second identification unit for identifying one or more initial first connected domains in the binary image; a first selecting unit for selecting an initial first connected domain having the largest area among the one or more initial first connected domains; a second determining unit for determining whether the selected initial first connected domain indicates a head region, based on an aspect ratio of the selected initial first connected domain and a second predefined threshold; a morphological opening operation unit for performing a morphological opening operation on the first binary image to obtain a residual binary image and a resulting binary image, the residual binary image being a binary image to be removed from the first binary image by performing the morphological opening operation and the resulting binary image being a result image of the morphological opening operation, if it is determined that the selected initial first connected domain does not indicate the head region; and a second deriving unit for deriving the second binary image, based on the resulting binary image.

According to this embodiment, a morphological opening operation is performed on a binary image obtained from each axial tomographic image of the subject if it is determined that the axial tomographic image does not show a head region of the subject. The morphological opening operation may remove small objects from the foreground of an image corresponding to the imaged subject. In this embodiment, the morphological opening operation may possibly remove small connections among different parts and then make the subsequent identification of connected domains more feasible.

Furthermore, the morphological opening operation is performed only when it is determined that the axial tomographic image does not show a head region of the subject, thereby avoiding removing small structures in the head region of the subject.

In this embodiment, the first recognizing unit may recognize a region corresponding to the residual binary image in the axial tomographic image. In this way, the residual binary image may be recorded in the first recognizing unit as belonging to the non-body part in the axial tomographic image and used for further removing non-body parts.

In a further embodiment, the first deriving unit further comprises a third identification unit for identifying one or more second connected domains in the residual binary image; a second feature quantity calculation unit for deriving, for each of the identified one or more second connected domains, a circularity parameter indicating a circularity of the second connected domain; a third determining unit for determining, for each of the identified one or more second connected domains, whether the second connected domain belongs to the non-body part, based on the derived circularity parameter of the second connected domain and the first predefined threshold; a first removing unit for removing all of the one or more second connected domains determined as belonging to the non-body part to obtain a third binary image; and a third deriving unit for deriving the second binary image, based on a combination of the third binary image and the resulting binary image, wherein the first recognizing unit is further adapted to recognize one or more regions corresponding to all of the one or more second connected domain(s) determined as belonging to the non-body part in the axial tomographic image.

According to this embodiment, it is determined whether any one of the image parts removed by the morphological opening operation belong to the body part of the subject, and if the answer is affirmative, said one or more image parts are added back to the binary image, thereby avoiding incompleteness of the body part of the subject resulting from the morphological opening operation.

In a still further embodiment, the image processing apparatus may comprise a second selecting unit for selecting a first connected domain having a largest area among all of the one or more first connected domains determined as not belonging to the non-body part, and a fourth determining unit for determining whether the selected first connected domain indicates a shoulder region, based on an aspect ratio of the selected first connected domain and a third predefined threshold, wherein the first recognizing unit is adapted to recognize a region corresponding to a head holder by matching a template of the head holder with the region in the axial tomographic image if it is determined that the selected first connected domain indicates the shoulder region.

According to the embodiment, even in the case of a shoulder region in which a head holder is tightly fitted, the head holder may be mistaken for a contour of a surface of a subject.

In addition, there provides a computer tomographic imaging system comprising an imaging acquisition apparatus for acquiring an axial tomographic image of an object and an imaging processing apparatus for processing the axial tomographic image, as described above.

Furthermore, there provides a method of processing an axial tomographic image of an object to recognize a non-body part in the axial tomographic image. The method comprises: (a) converting the tomographic image into a first binary image; (b) identifying one or more first connected domains in a second binary image, the second binary image being the first binary image or an image derived from the first binary image; (c) deriving, for each of the identified one or more first connected domains, a circularity parameter indicating a circularity of the first connected domain; (d) determining, for each of the identified one or more first connected domains, whether the first connected domain belongs to the non-body part, based on the derived circularity parameter of the first connected domain and a first predefined threshold; and (e) recognizing one or more regions corresponding to all of the one or more first connected domains determined as belonging to the non-body part in the axial tomographic image.

In another aspect, there provides an apparatus for recognizing a head region in a CT lateral image of a subject. In accordance with an embodiment of the present invention, the apparatus comprises a deriving unit for deriving a first image representing a bone of the subject from the CT lateral image; an extracting unit for extracting a boundary curve indicating an outer contour of a region comprising at least part of the occipital bone and at least part of the cervical vertebra of the subject in the first image; and a determining unit for determining a first pixel position indicating a bottommost point of the head region of the subject, based on a shape feature parameter of the boundary curve.

Herein, the bone of the subject refers to one or more pieces of bones of the subject contained in the CT lateral image. The person skilled in the art would appreciate that the outer contour of a region comprising at least part of the occipital bone and at least part of the cervical vertebra is part of the rear (i.e. posterior) side outer contour of the bone of the subject, namely the outer contour of the bone of the subject, viewed from the rear (i.e. posterior) to the front (i.e. anterior) of the subject.

The determining unit further comprises a first detecting unit for detecting a local extremum point of the boundary curve, the local extremum point having a local minimum coordinate along an axis corresponding to posterior anatomical direction of the subject, and a first determining unit for determining the detected local extremum point as the first pixel position indicating the bottommost point of the head region of the subject.

As regards the apparatus for recognizing the head region in the CT lateral image of the subject, it focuses on determining the bottommost point of the head region of the subject automatically, since it may be relatively easy to determine a topmost point of the head region. In particular, the bottommost point of the head region of the subject is determined based on a shape feature parameter of a boundary curve indicating an outer contour of a region comprising at least part of the occipital bone and at least part of the cervical vertebra of the subject in the CT lateral image. More particularly, the bottommost point of the head region of the subject is determined based on a local extremum point of the boundary curve corresponding to an anatomical location on the occipital bone and immediately adjacent to the cervical vertebra. In this way, the bottommost point of the head region of the subject may be determined automatically.

In one embodiment of the invention, the apparatus for recognizing the head region in the CT lateral image of the subject may also include a second detecting unit for detecting a second pixel position indicating a topmost point of the head region of the subject in the first image, the extracting unit extracting the boundary curve, based on the second pixel position; and wherein the determining unit further comprises a second determining unit for determining a detecting start point being at a predefined distance from the second pixel position, wherein the first detecting unit detects the local extremum point of the boundary curve, based on the determined detecting start point.

In this embodiment, since the local extremum point expected to be detected in the boundary curve may be detected starting from the detecting start point of the boundary curve, the detecting start point is much closer to the local extremum point expected to be detected as compared to the second pixel position, enabling the detection of the local extremum point of the boundary curve to be simplified and thus time saving.

Various aspects and features of the disclosure are described in further detail below. And other objects and advantages of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, wherein.

Figure 1:
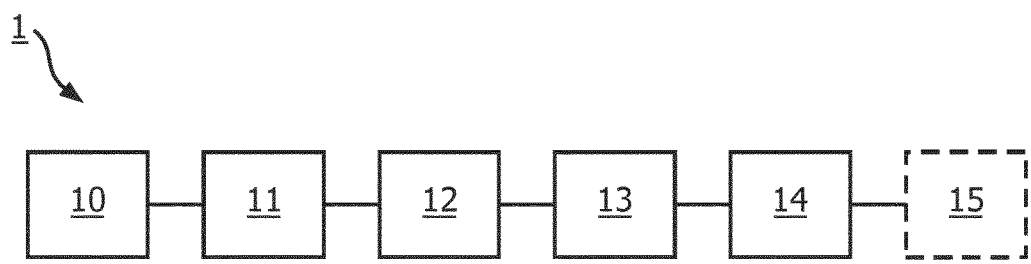
FIG. 1 illustrates an image processing apparatus for recognizing non-body part in an axial tomographic image.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

FIG. 1 illustrates an image processing apparatus 1 for recognizing non-body part in an axial tomographic image. During CT imaging, a plurality of axial tomographic images are acquired one by one and then a volume image may be reconstructed based on the plurality of axial tomographic images. The image processing apparatus 1 may process each axial tomographic image of a subject in real time to recognize a non-body part in the axial tomographic image, thereby obtaining a plurality of new axial tomographic images in which the non-body parts are removed. The volume image may be reconstructed based on the plurality of new axial tomographic images.

The image processing apparatus 1 may comprise a binarization unit 10, a first identification unit 11, a first feature quantity calculation unit 12, a first determining unit 13, and a first recognizing unit 14. Optionally, the image processing apparatus 1 may comprise a removing unit 15, which is shown in FIG. 1 by means of dashed lines.

The binarization unit 10 receives each axial tomographic image of a subject and converts it into a first binary image, the first binary image may be used to derive a second binary image in a first deriving unit 100, which may be described below, or, the first binary image may be used as the second binary image by itself.

The first identification unit 11 receives the second binary image, which may be the first binary image from the binarization unit 10 or the second binary image derived in the first deriving unit 100, which may be described below. One or more first connected domains are identified from the second binary image in the first identification unit 11. The one or more first connected domains may correspond to one or more body parts or one or more non-body parts in the axial tomographic image of the subject. It may be well known how to identify a connected domain from an image. Usually, the identification of the connected domain may be based on pixel values of the image. In an embodiment, it may be possible to set each pixel value in each of the one or more first connected domains as a uniform value and then mark the one or more first connected domains.

The one or more first connected domains are input to the first feature quantity calculation unit 12 in which a circularity parameter indicating a circularity of the first connected domain is derived for each of the identified one or more first connected domains. Generally, the circularity parameter may be derived based on the ratio between the inscribed and the circumscribed circles, i.e. the maximum and minimum sizes for circles that are just sufficient to fit inside and to enclose the shape of the identified first connected domain.

The detailed calculation of the circularity parameter may be well known in the field of mathematics.

The first determining unit 13 receives the circularity parameter of each of the identified one or more first connected domains and then determines, for each of the identified one or more first connected domains, whether the first connected domain belongs to a non-body part, based on the circularity parameter of the first connected domain and a first predefined threshold. The first predefined threshold may be selected in advance by referring to the circularity parameters of the non-body parts, such as a bed board or a head holder, and the circularity parameters of the body parts, such as head, shoulder, etc.

If it is determined that a first connected domain belongs to the non-body part, the first recognizing unit 14 recognizes a region corresponding to the first connected domain in the axial tomographic image. Finally, the first recognizing unit 14 may recognize all regions corresponding to all first connected domains determined as belonging to the non-body part in the axial tomographic image.

Optionally, the removing unit 15 removes all recognized regions in the first recognizing unit 14, including any recognized region corresponding to first connected domains, determined as belonging to the non-body part from the axial tomographic image. The removed axial tomographic image may be used for further reconstruction of the volume image of the subject.

Figure 2:
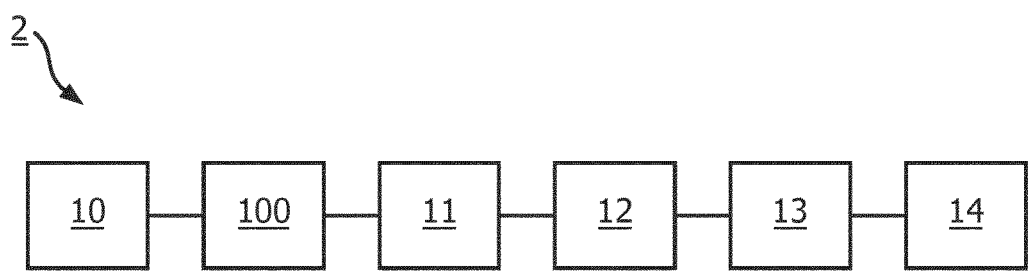
FIG. 2 illustrates an image processing apparatus for recognizing non-body part in an axial tomographic image, wherein the imaging processing apparatus includes a first deriving unit.

FIG. 2 illustrates an embodiment in which the image processing apparatus 2 comprises a first deriving unit 100 for deriving the second binary image as described above from the first binary image. The first deriving unit 100 is connected between the binarization unit 10 and the first identification unit 11. Detailed configurations of the first deriving unit 100 are shown in FIGS. 3 and 4.

In this embodiment, it is possible to perform a morphological opening operation on the first binary image to remove some small connections among different parts in the axial tomographic image before identifying the one or more first connected domains, resulting in different mutually connected parts in the axial tomographic image possibly being separated from each other, thereby avoiding that the different parts are identified as one first connected domain in the following operation of the first identification unit 11.

Taking into consideration that the head of a subject may include some small structures, such as those in nose or ear, which may be removed by the morphological opening operation, it is preferable that the morphological opening operation does not act on the head region of the subject. It may be expected to recognize the head region of the subject by means of its aspect ratio.

Figure 3:
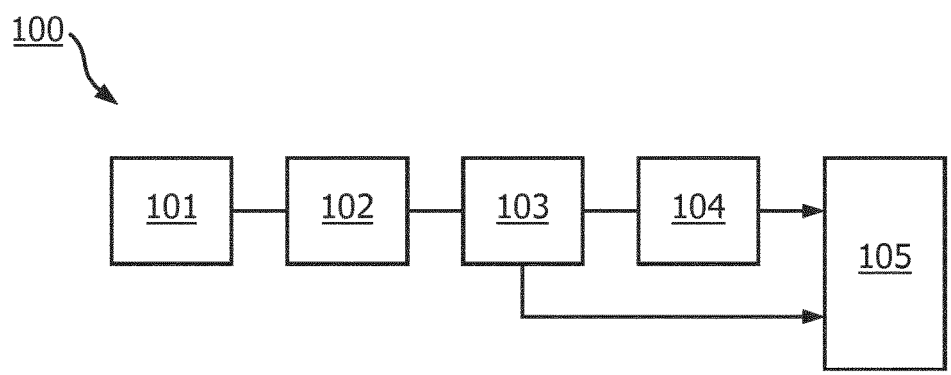
FIG. 3 illustrates a configuration of the first deriving unit of FIG. 2.
Figure 4:
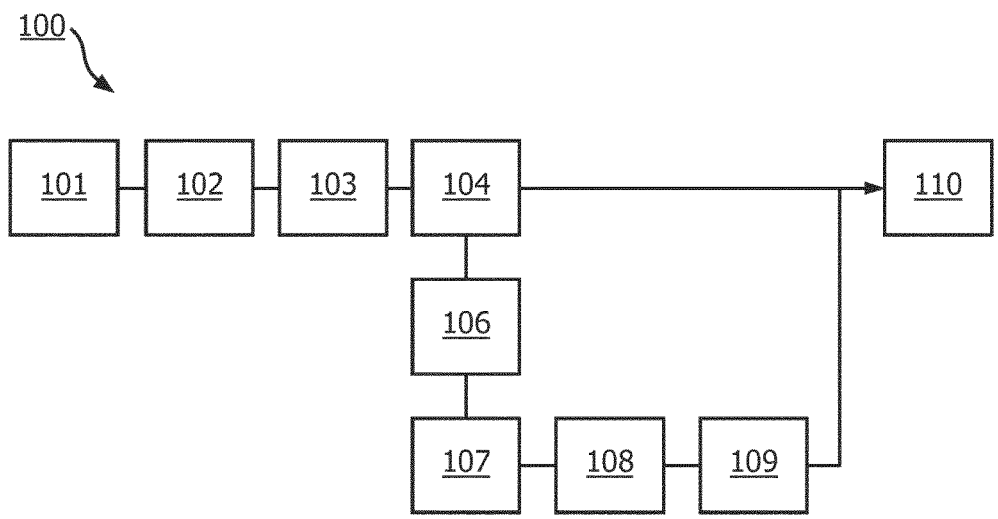
FIG. 4 illustrates another configuration of the first deriving unit of FIG. 2.

The exemplary first deriving unit 100 shown in FIG. 3 comprises a second identification unit 101, a first selecting unit 102, a second determining unit 103, a morphological opening operation unit 104 and a second deriving unit 105.

The second identification unit 101 receives the binary image from the binarization unit 10 and identifies one or more initial first connected domains in the binary image. The first selecting unit 102 selects an initial first connected domain having a largest area among the one or more initial first connected domains. The second determining unit 103 determines whether the selected initial first connected domain indicates a head region, based on an aspect ratio of the selected initial first connected domain and a second predefined threshold. The aspect ratio may be calculated based on a ratio between a height and a width of the selected initial first connected domain. Other calculation methods may also be contemplated. The second predefined threshold may be determined in advance by referring to a general aspect ratio of the head of the subject.

Based on the above units 101, 102 and 103, it may be identified whether the axial tomographic image shows the head of the subject by determining whether an initial first connected domain having a largest area indicates a head region based on an aspect ratio of the selected initial first connected domain and a second predefined threshold.

If it is determined that the initial first connected domain indicates the head region, i.e., the axial tomographic image shows the head of the subject, then, in order to avoid removing small structures from the head region, the morphological opening operation will not be executed on the axial tomographic image. The second deriving unit 105 receives the determination result from the second determining unit 103 and sets the first binary image to the second binary image.

If it is determined that the initial first connected domain does not indicate the head region, i.e., the axial tomographic image does not show the head of the subject, then, the morphological opening operation unit 104 performs a morphological opening operation on the first binary image to obtain a residual binary image and a resulting binary image, the residual binary image being a binary image to be removed from the first binary image by performing the morphological opening operation and the resulting binary image is a result image of the morphological opening operation. In this case, the second deriving unit 105 derives the second binary image, based on the resulting binary image.

In this case, the regions corresponding to the residual binary image may be recognized in the first recognizing unit 14 as belonging to non-body parts and are subsequently removed from the axial tomographic image in the removing unit 15.

Since the residual binary image may also include body parts, in order to avoid the region corresponding to the body parts in the residual binary image mistakenly being removed in the embodiment of FIG. 4 of the first deriving unit 100, it may be preferred that a further embodiment, also comprise a third identification unit 106, a second feature quantity calculation unit 107, a third determining unit 108, a first removing unit 109 and a third deriving unit 110 for processing the residual binary image before recognizing it in the first recognizing unit 14 as belonging to non-body parts. In this case, the residual binary image is processed to determine whether it still includes body parts.

The third identification unit 106 identifies one or more second connected domains in the residual binary image. The second feature quantity calculation unit 107 derives, for each of the identified one or more second connected domains, a circularity parameter indicating a circularity of the second connected domain. The third determining unit 108 determines, for each of the identified one or more second connected domains, whether the second connected domain belongs to the non-body part, based on the derived circularity parameter of the second connected domain and the first predefined threshold, as defined previously. The first removing unit 109 removes all of the one or more second connected domains determined as belonging to the non-body part to obtain a third binary image. The third deriving unit 110 derives the second binary image, based on a combination of the third binary image and the resulting binary image.

In this case, the first recognizing unit 14 also recognizes one or more regions corresponding to all of the one or more second connected domains determined as belonging to the non-body part in the axial tomographic image. The one or more recognized regions may be removed from the axial tomographic image in the removing unit 15.

According to the embodiment, it is determined whether or not the residual binary image still includes non-body parts, based on the circularity parameter of a connected domain corresponding to each part in the residual binary image, and the non-body parts are excluded from the residual binary image and the body parts remain included therein. By combining the residual binary image from which the non-body parts have been excluded with the resulting image of the morphological opening operation, the body parts in the residual binary image may be added back to the resulting image, thereby avoiding that body parts are mistakenly removed by the morphological opening operation.

Please note that, in this embodiment, the non-body parts excluded from the residual binary image may be recognized in the first recognizing unit 14 and are subsequently removed from the axial tomographic image in the removing unit 15.

Figure 5:
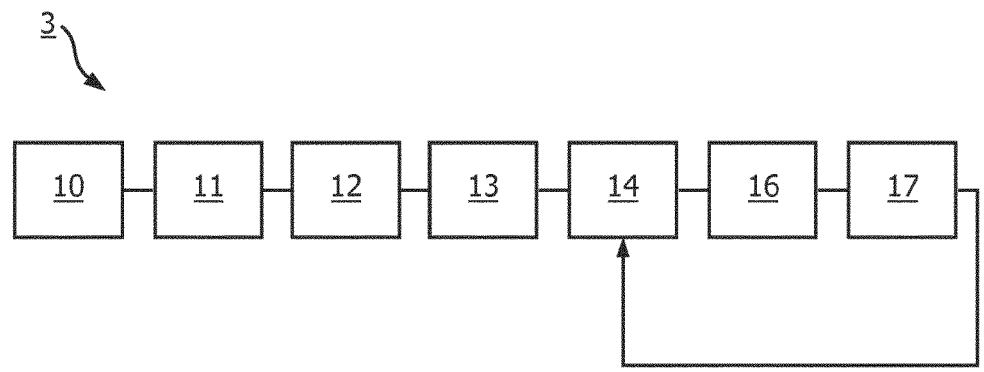
FIG. 5 illustrates an image processing apparatus for non-body part in an axial tomographic image.

FIG. 5 illustrates a further embodiment of an image processing apparatus 3 for recognizing non-body part in an axial tomographic image. The image processing apparatus 3 is different from the image processing apparatus 1 in FIG. 1 in that it includes a second selecting unit 16 and a fourth determining unit 17.

The second selecting unit 16 receives all of the one or more first connected domains determined as not belonging to the non-body part from the first recognizing unit 14 and selects a first connected domain having a largest area among all of the one or more first connected domains determined as not belonging to the non-body part.

The fourth determining unit 17 determines whether the selected first connected domain indicates a shoulder region, based on an aspect ratio of the selected first connected domain and a third predefined threshold. The third predefined threshold may be predefined by referring to a general aspect ratio of the shoulder of the subject.

The first recognizing unit 14 recognizes a region corresponding to a head holder by matching a template of the head holder with the region in the axial tomographic image if it is determined that the selected first connected domain indicates the shoulder region.

In this embodiment, the head holder may be removed by template matching for the shoulder region in which the head holder is a tight fit to the skin of the subject.

Although the image processing apparatus is described as hereinabove by referring to the embodiments shown in FIGS. 1-5 separately, it is contemplated that it may be advantageous to combine the embodiments with each other. For example, the embodiments shown in FIG. 5 may be combined with the embodiment shown in FIG. 2.

In addition, although the image processing apparatus is described above by referring to different units, it is contemplated that this is not a limitation, because one or more units may be combined to fulfill a same function.

It may also be contemplated that the first, second, or third predefined threshold is a value or a value range.

The terms "first", "second", "third" or "fourth" in the description are used to identify the units only and do not indicate any ordering.

It may be further contemplated that any one of the image processing apparatus 1, 2 and 3 as described above may be incorporated into a computer tomographic imaging system together with an image acquisition apparatus for acquiring an axial tomographic image of an object to process the axial tomographic image.

Figure 6:
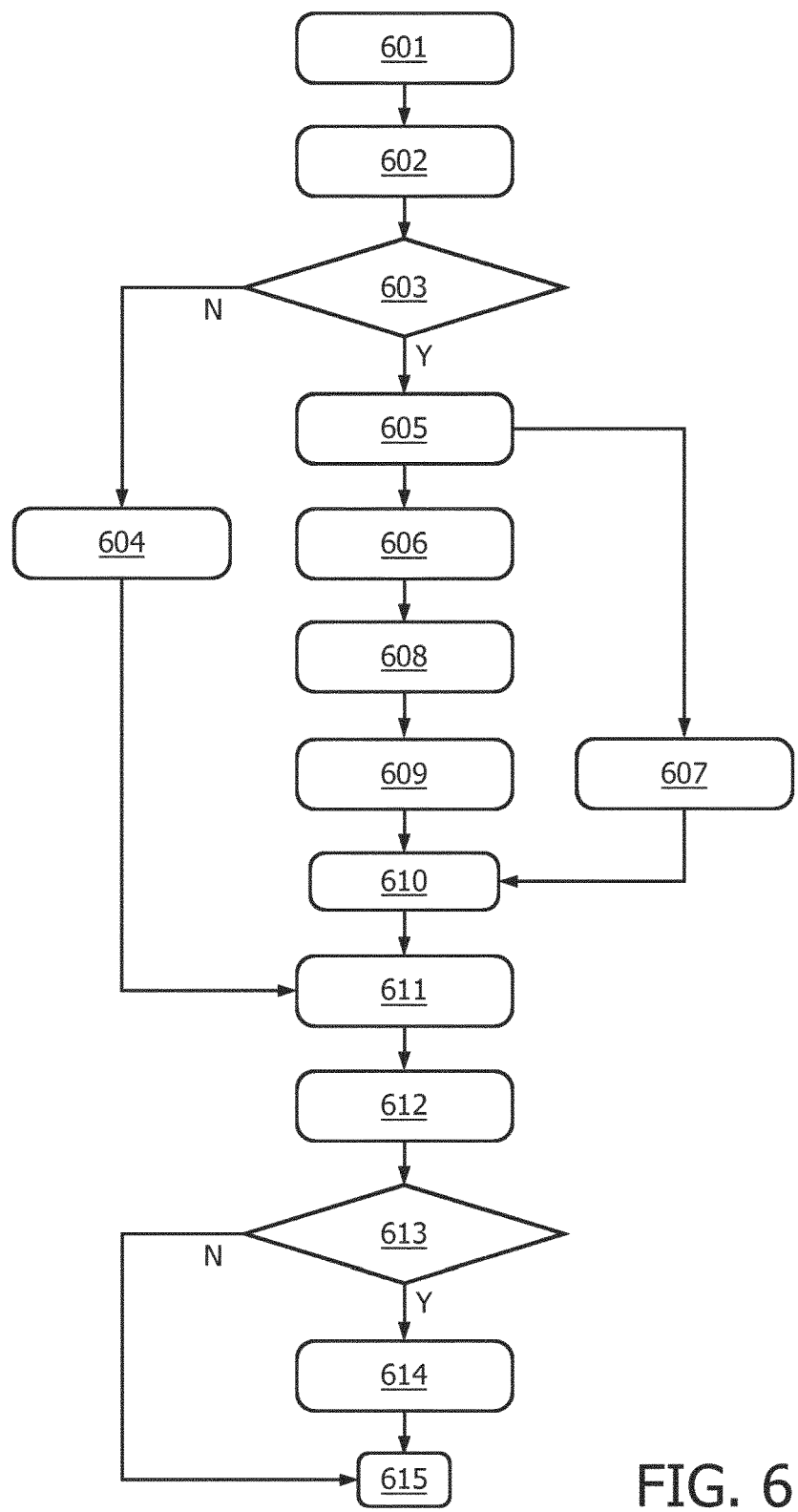
FIG. 6 illustrates a flowchart showing a detailed method of processing an axial tomographic image of a subject to recognize a non-body part in the axial tomographic image.

FIG. 6 illustrates a detailed method 600 of processing an axial tomographic image of a subject to recognize a non-body part in the axial tomographic image.

In step 601, an axial tomographic image of a subject is input to the image processing apparatus.

In step 602, the tomographic image is converted to a first binary image.

In step 603, it is determined whether or not a morphological opening operation may be performed on the first binary image.

In particular, one or more initial first connected domains are identified from the first binary image. An initial first connected domain having a largest area is selected among the one or more initial first connected domains of the binary image. Based on an aspect ratio of the selected initial first connected domain and a second predefined threshold, it is determined whether the selected initial first connected domain indicates a head region of a subject. In order to avoid that the morphological opening operation removes small structures from the axial tomographic image showing the head region of the subject, the morphological opening operation will not be performed on the axial tomographic image showing the head region of the subject.

If it is determined that the selected initial first connected domain indicates the head region, i.e., the axial tomographic image shows the head region, the first binary image is set to a second binary image in step 604 and the method proceeds to a step 611.

If it is determined that the selected initial first connected domain does not indicate the head region, i.e., the axial tomographic image does not show the head region, the method proceeds to a step 605.

In step 605, a morphological opening operation is performed on the first binary image obtained in step 602 to obtain a residual binary image in step 606 and a resulting binary image in step 607. The residual binary image is a binary image to be removed from the first binary image by performing the morphological opening operation and the resulting binary image is a result image of the morphological opening operation.

In step 608, one or more second connected domains are identified in the residual binary image.

In step 609, all of the one or more second connected domains determined as belonging to the non-body part, based on the derived circularity parameter of each of the one or more second connected domains and the first predefined threshold, are removed from the residual binary image, resulting in a third binary image. In this step, the region(s) corresponding to all of the one or more second connected domains determined as belonging to the non-body part may be recognized in the axial tomographic image.

In step 610, a second binary image is derived from a combination of the resulting binary image in step 607 and the third binary image.

In step 611, one or more first connected domains are identified in the second binary image. The second binary image may be obtained from step 604 or step 610. In particular, the first connected domains may be identified by setting each pixel value in each of the one or more first connected domains as a uniform value and marking the one or more first connected domains.

In step 612, it is determined, for each of the identified one or more first connected domains, whether the first connected domain belongs to the non-body part, based on a circularity parameter of the first connected domain and a first predefined threshold, thereby recognizing all first connected domains determined as belonging to the non-body part in the axial tomographic image. In this step, the region(s) corresponding to all the recognized first connected domains may be recognized in the axial tomographic image also.

In step 613, it is determined whether the axial tomographic image indicates a shoulder region of a subject, based on an aspect ratio of a selected first connected domain having a largest area among all of the one or more first connected domains determined as not belonging to the non-body part and a third predefined threshold.

If it is determined that the selected first connected domain indicates the shoulder region in the step 613, in step 614, a region corresponding to a head holder may be recognized by matching a template of the head holder with the region in the tomographic image. Otherwise, the method will end at step 615.

It may be contemplated to combine/divide any of the above steps of the method to fulfill the same function; the steps described above are not limited.

It may also be contemplated that in step 615 all the regions recognized as belonging to the non-body parts are removed from the axial tomographic image.

It may further be contemplated that one or more steps in the claims may be omitted. For example, the steps 605-610 may be omitted when the axial tomographic image indicates a head region of a subject. Those skilled in the art may conceive variations of the method with reference to the description of the image processing apparatus of the application.

Figure 7:
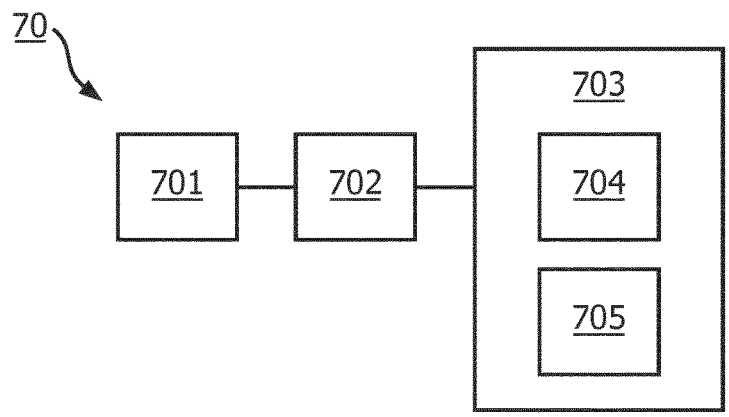
FIG. 7 illustrates an apparatus for recognizing a head region in a CT lateral image of a subject according to an embodiment of the invention.

In an aspect of the present invention, there provides an apparatus for automatically recognizing the head region in a CT lateral image of a subject, as shown in FIG. 7. The apparatus 70 may include a deriving unit 701, an extracting unit 702, and a determining unit 703.

Figure 8:
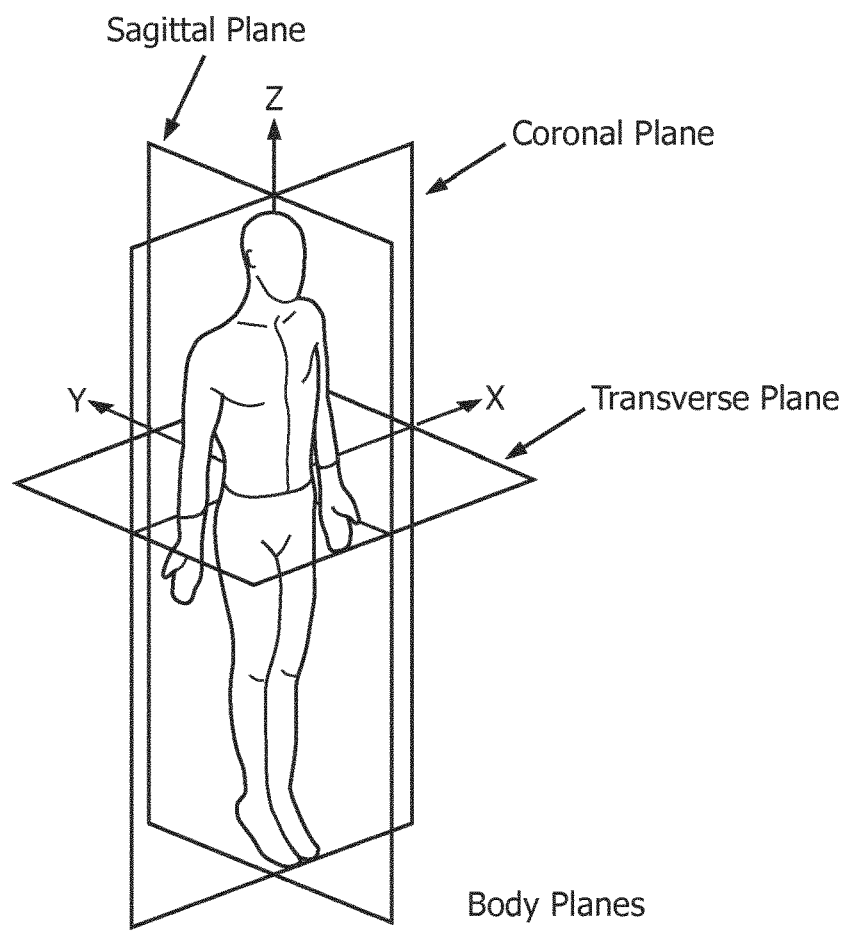
FIG. 8 is a diagram of standard anatomical position defined for human anatomy.

FIG. 8 is a diagram of a standard anatomical position defined for human anatomy in CT imaging, wherein the x axis corresponds to the left anatomical direction, the y axis corresponds to the posterior anatomical direction, and the z axis corresponds to the superior anatomical direction. It may be clearly shown in this figure that in a three-dimensional (3D) Cartesian coordinate system for CT imaging, the lateral image of the subject corresponds to the y/z plane (often called sagittal plane), an axial image of the subject corresponds to the x/z plane (often called coronal plane or frontal plane), and a transverse image corresponds to the x/y plane (often called transverse plane or cross-sectional plane). The lateral image can be an image of a sagittal plane passing through the body acquired by means of volume scanning, or can be a projection image, such as a scout image (also called surview image) acquired by means of a scout scanning (also called surview scanning).

Figure 9:
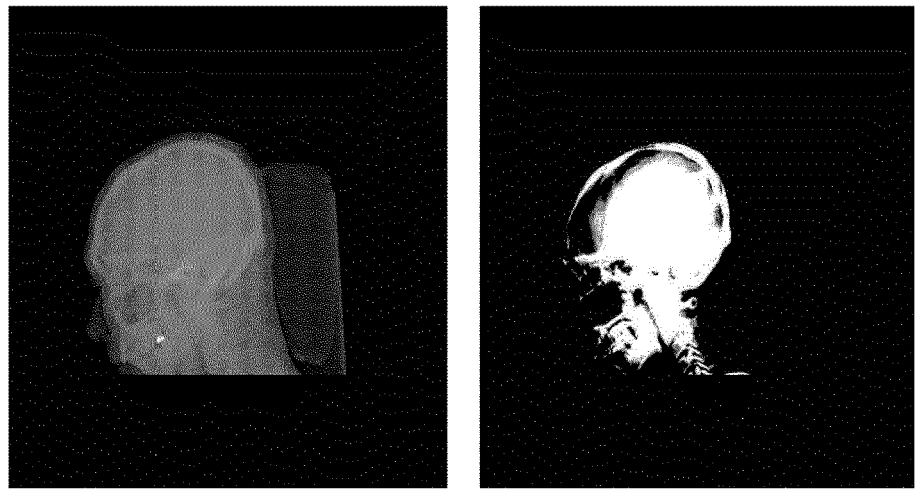
FIG. 9 illustrates an original CT lateral image (left) and a derived first image (right) according to an embodiment of the invention.

Returning to FIG. 7, the deriving unit 701 receives the CT lateral image of the subject which corresponds to the y/z plane in the 3D Cartesian coordinate system for CT imaging. The CT lateral image may be processed to remove non-body parts therefrom or change an orientation of an imaged object in the CT lateral image before it is sent to the deriving unit 701 for further processing. In particular, each of the CT lateral images of the subject to be sent to the deriving unit 701 may be processed to locate the head of the subject in a same orientation, for example, the orientation as shown in FIG. 9. The description will be given below with reference to the orientation of the head of the subject shown in FIG. 9, however, this is not a limitation.

The deriving unit 701 derives a first image representing a bone of the subject from the CT lateral image. This may be achieved by the gray transformation of the CT lateral image of the subject and segmentation of the bone of the subject.

In particular, each pixel value of the CT lateral image of the subject may be transformed into a gray scale range from 0-255. A histogram may be generated for the transformed CT lateral image of the subject and the pixel values representing a bone of the subject may be derived by means of a segmentation method based on the histogram. Please note that this is not a limitation, those skilled in the art may conceive other methods to derive the pixel values representing a bone of the subject. After the operation of the deriving unit 701, only a skull of the subject is left in the first image. FIG. 9 illustrates an original CT lateral image (left) and a derived first image (right).

Figure 10:
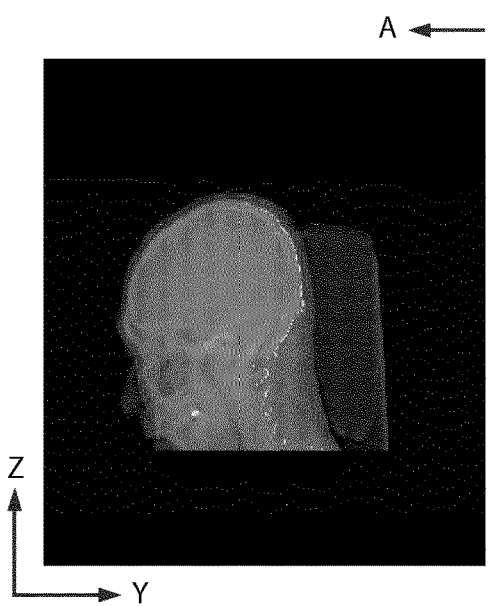
FIG. 10 illustrates an extracted boundary curve in the original CT lateral image according to the invention.

The extracting unit 702 receives the first image from the deriving unit 701 and extracts a boundary curve indicating an outer contour of a region comprising at least part of occipital bone and at least part of cervical vertebra of the subject in the first image. The boundary curve may be shown in the original CT lateral image of the subject. FIG. 10 illustrates the extracted boundary curve indicating an outer contour of a region comprising at least part of occipital bone and at least part of cervical vertebra of the subject. Please note that the boundary curve may be a set of pixel points composed by both pixel points indicative of the outer contour of the occipital bone and pixel points indicative of the outer contour of and the cervical vertebra of the subject in the CT lateral image.

There are many methods that may be used to extract the set of pixel points of the boundary curve. In one embodiment, each pixel point of the set of pixel points may be selected as a point at which, firstly, the pixel value exceeds a predetermined pixel threshold value. By referring to FIG. 10, for each row of pixels in the CT lateral images, the pixel point of the set for the row of pixels may be searched along a direction A, namely a direction from posterior (rear) to anterior (front).

In another embodiment, an edge detection method based on the gradient of pixel values of pixels of the CT lateral image may be used. In this method, a start point on the boundary curve shall be predefined. For example, the start point may be a topmost point of the head (which is described below). Starting from the start point, the pixel value of each pixel is compared with adjacent pixels. Points may be determined to be pixel points of the boundary curve if the gradient value between each point and adjacent points thereof meets a predefined criterion. In view of the CT lateral image shown in FIG. 10, the pixel point of the boundary curve may be searched starting from the topmost point of the head of the subject and towards the right and downward along a direction proximate to the scalp of the head.

The edge detection method based on the gradient may be known by those skilled in the art. The above description is only illustrative; those skilled in the art may use any such method known in the prior art.

The determining unit 703 receives the extracted boundary curve and determines a first pixel position indicating a bottommost point of the head region of the subject, based on a shape feature parameter of the boundary curve.

The determining unit 703 may further include a first detecting unit 704 for detecting a local extremum point of the boundary curve, the local extremum point has a local minimum coordinate along an axis (i.e. the Y axis) corresponding to posterior anatomical direction of the subject. The determining unit 703 further comprises a first determining unit 705 for determining the detected local extremum point as the first pixel position indicating the bottommost point of the head region of the subject. The detection of the local extremum point of the boundary curve may be achieved by means of a plurality of methods well known in the art, for example based on the curve's slope.

Figure 11:
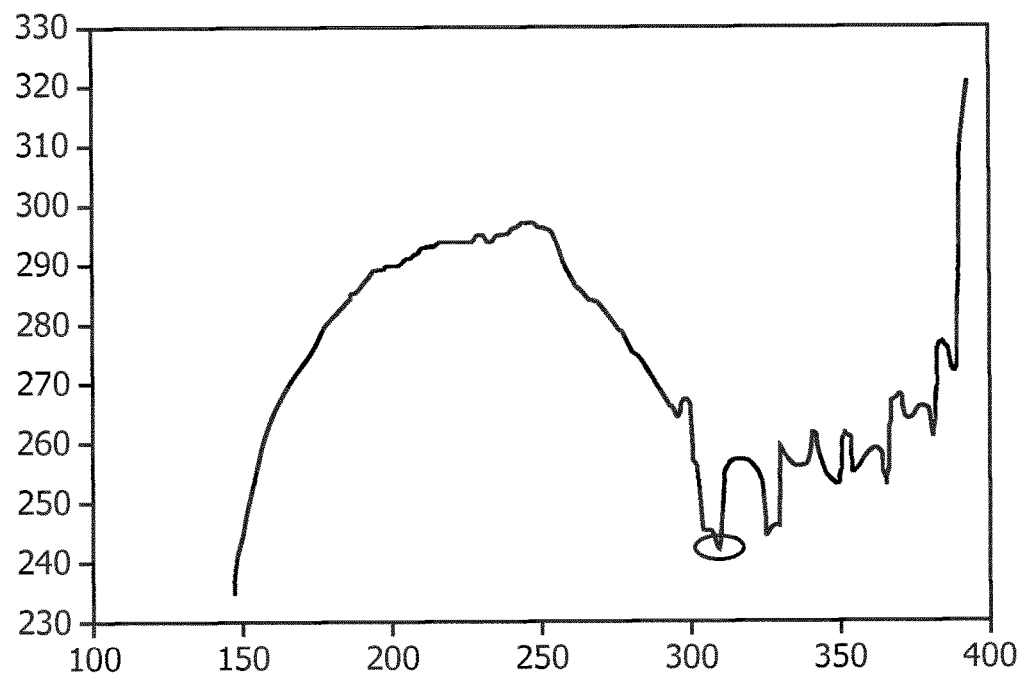
FIG. 11 illustrates an extracted boundary curve which is obtained by rotating 90° from that shown in FIG. 9.

The inventors of the present invention recognized that such local extremum point of the boundary curve corresponds to an anatomical location on the occipital bone and is immediately adjacent to the cervical vertebra of the subject, and therefore may be determined as being a bottommost point of the head region of the subject. FIG. 11 shows the extremum point of the boundary curve to be determined in the first determining unit 705. In FIG. 11, for illustration purpose, the boundary curve is obtained by rotating the boundary curve shown in FIG. 10 by 90° counter clockwise. Consequently, the vertical axis in FIG. 11 is the y-axis in FIG. 10. In this case, the extremum point of the boundary curve to be determined in the first determining unit 705 may be is a local minimum point of the boundary curve, wherein the local minimum point has a local minimum y coordinates. In some embodiments, the first local minimum point of the boundary curve, namely the local minimum point which has the largest z coordinates among all the local minimum point of the boundary curve, is determined as the extremum point of the boundary curve.

Figure 12:
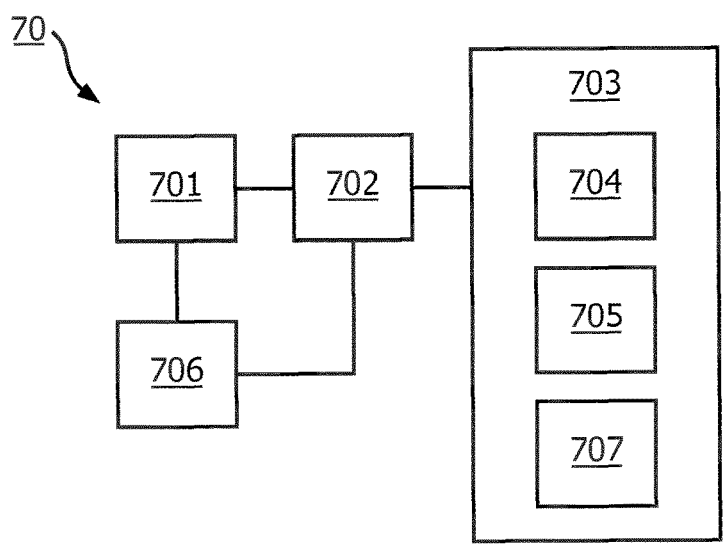
FIG. 12 illustrates an apparatus for recognizing a head region in a CT lateral image of a subject according to an embodiment of the invention.

With reference to FIG. 12, in which a second detecting unit 706 is further included in the apparatus 70, an embodiment for detecting the local extremum point determined as being the topmost point of the head region of the subject is described in detail. The units in the embodiment, which have the same reference signs as in FIG. 7, may fulfill the same function.

In this embodiment, the second detecting unit 706 receives the first image from the deriving unit 701 and detects a second pixel position indicating a topmost point of the head region of the subject in the first image. This may be achieved by a plurality of methods.

One of the methods aims is to detect the second pixel position indicating the topmost point of the head region by horizontal and vertical projection of the first image. In the horizontal projection of the first image, a H coordinate of the second pixel position in the first image may be determined as a first non-zero point of the projection; while in the vertical projection of the first image, a V coordinate of the second pixel position in the first image may be determined by finding a position having a maximum projection value among the vertical projections of the first image and recognizing a V coordinate corresponding to the found position as the V coordinate of the second pixel position.

Please note that in order to distinguish from the three-dimensional (3D) Cartesian coordinate system for CT imaging as shown in FIG. 8, a two dimensional (2D) Cartesian coordinate system for the lateral image is defined with a H axis and a V axis, wherein the H axis corresponds to the z axis along a vertical direction shown in FIG. 10 and the V axis corresponds to the y axis along a horizontal direction shown in FIG. 10. Although a reference frame of the CT lateral image is described with reference to FIG. 10 only, it may be applied to any other CT lateral image.

Please note that the method described herein is not a limitation, those skilled in the art may contemplate other methods to determine the second pixel position indicating the topmost point of the head region also.

After the second pixel position indicating the topmost point of the head region is detected in the first image by the second detecting unit 706, the bottommost point of the head region may be detected along the boundary curve and may start from a detecting start point of the boundary curve being at a predefined distance from the second pixel position.

In this embodiment, the extracting unit 702 may extract the boundary curve, based on the second pixel position, for example, starting from the second pixel position and subsequently towards the occipital bone and cervical vertebra of the subject. In an embodiment, the determining unit 703 comprises a second determining unit 707 for determining the detecting start point based on the second pixel position. The detecting start point is at a predefined distance from the second pixel position in the boundary curve. In this case, the first detecting unit 704 may start its detection of the local extremum point in the boundary curve from the determined detecting start point in the boundary curve. The predefined distance may be selected by a user by referring to a general size of a subject from a topmost point of the head to a bottommost point of the head.

It may also be contemplated to select the predefined distance based on a size of the subject, or, based on the CT lateral image. For example, if the top of the head region is not shown in the CT lateral image, the predefined distance may be selected as being relatively small.

In this way, since the detecting start point is much closer to the local extremum point expected to be detected, as compared to the second pixel position, and thus the local extremum point expected to be detected in the boundary curve may be detected within a relatively small range starting from the detecting start point, the detection of the local extremum point of the boundary curve may be simplified. It may be contemplated to detect the local extremum point expected to be detected in the boundary curve in a range starting from the second pixel position indicating the topmost point of the head region of the subject in the first image also.

It may be contemplated that the first determining unit 705 may determine the second pixel position as a topmost point of the head region of the subject; a left border point and/or a right border point of the head region of the subject may be detected in the first determining unit 705 also by referring to the method for detecting the second pixel position. Based on the determined topmost point, bottommost point, left border point and right border point of the head region, it may be possible to recognize the head region in the original CT lateral image.

It may be contemplated that the local extremum point of the boundary curve to be determined as being the bottommost point of the head region may be a maximum point or a minimum point of the boundary curve according to the orientation of the head of the subject. For example, in FIG. 11, it is a first minimum point starting from the second pixel position.

It may be contemplated that the detection of the local extremum point of the boundary curve as described with reference to FIG. 12 is not a limitation, and those skilled in the art may modify the method to fulfill a same function as long as a local extremum point corresponding to an anatomical location on the occipital bone and immediately adjacent to the cervical vertebra is detected.

It may be also contemplated to include the apparatus for recognizing a head region in the CT lateral image of the subject in a computer tomographic imaging system together with an imaging acquisition apparatus for acquiring the CT lateral image of the subject.

Figure 13:
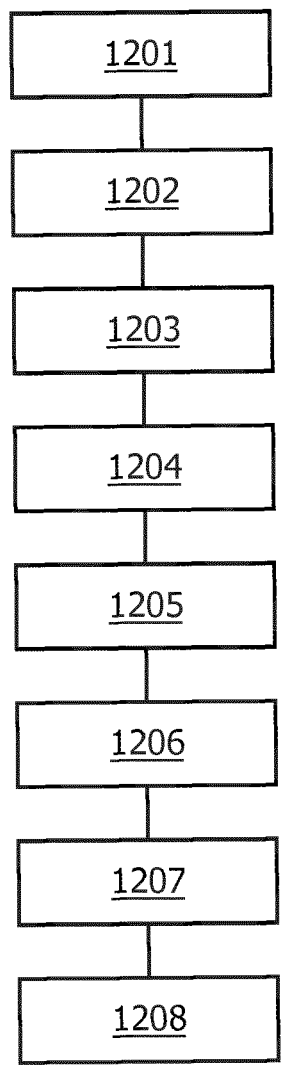
FIG. 13 illustrates a detailed flowchart of a method of recognizing a head region in a CT lateral image of a subject according to an embodiment of the invention.

Furthermore, in FIG. 13, a flowchart of a method 1200 for recognizing a head region in a CT lateral image of a subject is described.

In step 1201, the CT lateral image of the subject may be received by the apparatus for recognizing the head region in the CT lateral image of the subject.

In step 1202, a first image corresponding to a bone of the subject may be derived from the CT lateral image. The method for deriving the first image has been described above.

In step 1203, a second pixel position indicating a topmost point of the head region of the subject may be detected in the first image by means of horizontal and vertical projection of the first image.

In step 1204, a boundary curve indicating an outer contour of a region comprising at least part of the occipital bone and at least part of cervical vertebra of the subject may be extracted from the first image, preferably based on the second pixel position.

Optionally, in step 1205, a detecting start point in the boundary curve is determined based on the second pixel position indicating the topmost point of the head region of the subject, the detecting start point being at a predefined distance from the second pixel position.

In step 1206, a local extremum point corresponding to an anatomical location on the occipital bone and immediately adjacent to the at least part of cervical vertebra may be detected from the boundary curve. Optionally, the detection of the local extremum point expected to be detected may be based on—for example started from—the detecting start point.

In step 1207, the detected local extremum point is determined as a first pixel position indicating the bottommost point of the head region of the subject.

In step 1208, the head region of the subject in the CT lateral image is recognized based on the second pixel position indicating a topmost point of the head region of the subject and the first pixel position indicating the bottommost point of the head region of the subject.

It may be contemplated that any of the above steps or units may be combined with each other or further divided to fulfill a same function.

Please note that the image processing apparatus and the apparatus for recognizing a head region in a CT lateral image are not limited to those mentioned above. It will be apparent to those skilled in the art that the various aspects of the invention claimed may be practiced in other examples that depart from these specific details.

Furthermore, the mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the product claims enumerating several units, several of these units can be embodied by one and the same item of software and/or hardware. The usage of the words first, second and third, et cetera, does not indicate any ordering. These words are to be interpreted as names.

The invention claimed is:

1. An apparatus for recognizing a head region in a CT lateral image of a subject, comprising:
   a deriving unit for deriving a first image representing a bone of the subject from the CT lateral image;
   an extracting unit for extracting a boundary curve indicating an outer contour of a region comprising at least part of the occipital bone and at least part of the cervical vertebra of the subject in the first image; and
   a determining unit for determining a first pixel position indicating a bottommost point of the head region of the subject, based on a shape feature parameter of the boundary curve.

2. The apparatus of claim 1, wherein the determining unit comprises:
   a first detecting unit for detecting a local extremum point of the boundary curve, the local extremum point having a local minimum coordinate along an axis corresponding to posterior anatomical direction of the subject; and
   a first determining unit for determining the detected local extremum point as the first pixel position indicating the bottommost point of the head region of the subject.

3. A computer tomographic imaging system comprising:
   an imaging acquisition apparatus for acquiring a CT lateral image of a subject; and
   an apparatus for recognizing a head region in the CT lateral image of the subject according to claim 1.

4. A method for recognizing a head region in a CT lateral image of a subject, comprising:
   deriving a first image corresponding to a bone of the subject from the CT lateral image;
   extracting a boundary curve indicating an outer contour of a region comprising at least part of the occipital bone and at least part of the cervical vertebra of the subject in the first image; and
   determining a first pixel position indicating a bottommost point of the head region of the subject, based on a shape feature parameter of the boundary curve.

5. The method of claim 4, further comprising:
   detecting a local extremum point of the boundary curve, the local extremum point having a local minimum coordinate along an axis corresponding to posterior anatomical direction of the subject, and
   determining the detected local extremum point as the first pixel position indicating the bottommost point of the head region of the subject.

6. A non-transitory computer readable storage medium encoded with computer readable instructions, which, when executed by a processor of a computing system, causes the processor to:
   receive a CT lateral image of a subject;
   derive a first image representing a bone of the subject from the CT lateral image;
   extract a boundary curve indicating an outer contour of a region comprising at least part of the occipital bone and at least part of the cervical vertebra of the subject in the first image; and
   determine a first pixel position indicating a bottommost point of the head region of the subject, based on a shape feature parameter of the boundary curve.

7. The apparatus of claim 2, wherein the extracted boundary curve is plotted using a Cartesian coordinate system.

8. The apparatus of claim 2, further comprising:
   a second detecting unit for detecting a second pixel position indicating a topmost point of the head region of the subject, and wherein the determining unit further comprises;
   a second determining unit for detecting a start point in the boundary curve based on the second pixel position, wherein the detected local extremum point is based on the start point.

9. The apparatus of claim 8, wherein the start point is a predetermined distance from the second pixel.

10. The apparatus of claim 9, wherein the predetermined distance is based on a size of the subject.

11. The apparatus of claim 8, wherein the detected local extremum point is within a predetermined range away from the start point.

12. The apparatus of claim 9, wherein the first determining unit detects a left border point or a right border point of the head region based on the topmost point and identifies the head region in the original CT lateral image based on the left or right border point.

13. The method of claim 4, further comprising:
detecting a second pixel position indicating a topmost point of the head region of the subject; and
detecting a start point in the boundary curve based on the second pixel position, wherein the detected local extremum point is based on the start point.

14. The method of claim 13, wherein the start point is a predetermined distance from the second pixel.

15. The method of claim 14, wherein the predetermined distance is based on a size of the subject.

16. The method of claim 13, wherein the detected local extremum point is within a predetermined range away from the start point.

17. The method of claim 13, further comprising:
detecting a left border point or a right border point of the head region based on the topmost point; and
identifying the head region in the original CT lateral image based on the left or right border point.

18. The computer readable storage medium of claim 6, wherein executing the computer readable instructions further causes the processor to:
detect a local extremum point of the boundary curve, the local extremum point having a local minimum coordinate along an axis corresponding to posterior anatomical direction of the subject, and
determine the detected local extremum point as the first pixel position indicating the bottommost point of the head region of the subject.

19. The computer readable storage medium of claim 18, wherein executing the computer readable instructions further causes the processor to:
detect a second pixel position indicating a topmost point of the head region of the subject; and
detect a start point in the boundary curve based on the second pixel position, wherein the detected local extremum point is based on the start point.

20. The computer readable storage medium of claim 19, wherein executing the computer readable instructions further causes the processor to:
detect a left border point or a right border point of the head region based on the topmost point and identify the head region in the original CT lateral image based on the left or right border point.

* * * * *